United States Patent
Gellman

(10) Patent No.: US 6,699,214 B2
(45) Date of Patent: *Mar. 2, 2004

(54) SHEAR-SENSITIVE INJECTABLE DELIVERY SYSTEM

(75) Inventor: Barry N. Gellman, North Easton, MA (US)

(73) Assignee: SciMed Life Systems, Inc., Maple Grove, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/487,436

(22) Filed: Jan. 19, 2000

(65) Prior Publication Data

US 2003/0018298 A1 Jan. 23, 2003

(51) Int. Cl.⁷ .............................................. A61M 37/00

(52) U.S. Cl. ........................................ 604/82; 604/187

(58) Field of Search .............................. 604/32, 82, 83, 604/113, 89–91, 221, 181, 187

(56) References Cited

U.S. PATENT DOCUMENTS

| | | | |
|---|---|---|---|
| 346,265 A | * 7/1886 | Charlton et al. | 222/241 |
| 2,825,134 A | 3/1958 | Hicks | 32/17 |
| 2,888,923 A | 6/1959 | Reis | 128/218 |
| 3,602,950 A | 9/1971 | Bielfeldt | 18/12 |
| 3,732,858 A | * 5/1973 | Banko | 600/566 |
| 3,779,383 A | 12/1973 | Ayres | 210/84 |
| 3,788,003 A | * 1/1974 | Creighton et al. | 47/56 |
| 4,006,736 A | 2/1977 | Kranys et al. | 128/2 |
| 4,074,362 A | 2/1978 | Kruder et al. | 366/82 |
| 4,202,635 A | * 5/1980 | Hendrickson | 366/162.3 |
| 4,243,080 A | 1/1981 | Choksi et al. | 141/2 |
| 4,285,600 A | 8/1981 | Kruder | 366/89 |
| 4,542,176 A | 9/1985 | Graham | 524/543 |
| 4,649,919 A | * 3/1987 | Thimsen et al. | 606/80 |
| 4,803,075 A | 2/1989 | Wallace et al. | 424/423 |
| 4,929,238 A | 5/1990 | Baum | 604/208 |
| 5,071,040 A | * 12/1991 | Laptewicz, Jr. | 222/235 |
| 5,089,606 A | 2/1992 | Cole et al. | 536/54 |
| 5,104,380 A | 4/1992 | Holman et al. | 604/117 |
| 5,259,749 A | 11/1993 | Meixner et al. | 425/205 |
| 5,322,511 A | 6/1994 | Armbruster et al. | 604/155 |
| 5,360,410 A | 11/1994 | Wacks | 604/232 |

(List continued on next page.)

FOREIGN PATENT DOCUMENTS

| | | |
|---|---|---|
| DE | 545 878 | 2/1932 |
| DE | 33 17 536 | 11/1984 |
| FR | 2 572 677 | 5/1986 |
| WO | WO 94 15660 | 7/1994 |

*Primary Examiner*—Brian L. Casler
*Assistant Examiner*—Kevin C. Sirmons
(74) *Attorney, Agent, or Firm*—Testa, Hurwitz & Thibeault, LLP

(57) ABSTRACT

A delivery system for delivering a shear-sensitive injectable material into the body of a mammal, such as a human being, acts as a mechanical feed that continuously mixes a shear-sensitive injectable material as it delivers the shear-sensitive injectable material to a target tissue, or to a site adjacent a target tissue. In one embodiment of the invention, the delivery system comprises an injector system including a rotatable mixing member coupled to a driving system. The injector system comprises a housing defining a lumen and having an output end and a driving system connection end and includes a rotatable mixing member for coupling to the driving system and for mixing and delivering the shear-sensitive injectable material. The driving system comprises a drive mechanism, an actuator capable of actuating the drive mechanism, and an interfacing member coupled to the drive mechanism for coupling with the mixing member to rotate the mixing member when the interfacing member is driven by the drive mechanism.

16 Claims, 7 Drawing Sheets

U.S. PATENT DOCUMENTS

| | | | |
|---|---|---|---|
| 5,383,884 A | * 1/1995 | Summers | 606/170 |
| 5,395,326 A | 3/1995 | Haber et al. | 604/90 |
| 5,397,180 A | * 3/1995 | Miller | 366/338 |
| 5,423,799 A | * 6/1995 | Shiu | 606/159 |
| 5,458,475 A | 10/1995 | Suumen | 425/208 |
| 5,489,266 A | * 2/1996 | Grimard | 604/89 |
| 5,647,851 A | 7/1997 | Pokras | 604/131 |
| 5,653,692 A | * 8/1997 | Masterson et al. | 604/113 |
| 5,658,261 A | 8/1997 | Neer et al. | 604/240 |
| 5,674,195 A | 10/1997 | Truthan | 604/87 |
| 5,676,545 A | * 10/1997 | Jones | 433/165 |
| 5,724,994 A | 3/1998 | Simon et al. | 128/885 |
| 5,770,141 A | * 6/1998 | Schulte et al. | 264/311 |
| 5,842,782 A | 12/1998 | Lau | 366/85 |
| 5,865,798 A | * 2/1999 | Grimard et al. | 604/89 |
| 5,899,881 A | * 5/1999 | Grimard et al. | 604/89 |
| 6,033,105 A | * 3/2000 | Barker et al. | 366/182.3 |

\* cited by examiner

SHEAR-SENSITIVE INJECTABLE DELIVERY SYSTEM

TECHNICAL FIELD

The invention relates to a system for use in the delivery of a material into the body of a mammal and a method of using such a system. More particularly, the invention relates to a system for use in delivering a shear-sensitive injectable material into the body of a mammal to bulk-up, augment, or replace tissue.

BACKGROUND INFORMATION

Shear-sensitive injectable materials have a variety of medical applications. These materials may be used as bulking agents to strengthen tissues weakened by old age and/or disease, as implants to contour overlying tissue (e.g., in plastic surgery applications), or as prosthetic implants, acting as replacement tissue. In some instances, it is desirable to use a shear-sensitive injectable material as an embolic, for example, in the occlusion of abnormal blood vessels. Typical shear-sensitive injectable materials comprise a cross-linked polysaccharide or hydrogel, a carrier (typically a hydrophobic material such as oil), and matrix materials, providing paste-like compounds useful to bulk up tissue.

Current methods and delivery systems for delivering shear-sensitive injectable materials to a tissue, or to a space adjacent to a tissue, have certain disadvantages. A typical delivery system used is a syringe comprising a tube and a plunger. During the injection process, the carrier/hydrophobic material has a tendency to separate from the matrix material within the tube of the syringe, resulting in carrier-only injection into a tissue. Separation may be caused by a number of factors including shelf-life, material separation, excessive pressure in the syringe applied by the plunger, pushing the carrier/hydrophobic material ahead of the matrix material, or the use of an injection needle having a diameter which is too small. When a carrier is not well mixed, the matrix material is difficult to advance through the syringe with the plunger. Ultimately, the physician is unable to gauge properly the amount of bulking material he or she is actually injecting, resulting in the necessity for multiple treatments and discomfort to the patient.

SUMMARY OF THE INVENTION

It is an object of the present invention to provide a system for delivering a shear-sensitive injectable material. As defined herein, a "shear-sensitive injectable material" is a material which comprises components, or is itself a component, which is subject to shear (e.g., causing degradation or a change in viscosity) upon mixing and passage through a standard-sized needle (e.g., about 10 gauge to about 25 gauge). In the process of mixing, shear-sensitive injectable materials form paste-like compounds which are ideal for implantation into the body because they conserve their volume and do not migrate far from a site of injection. Such materials are useful in applications to bulk-up, augment, or replace tissues.

The present invention relates to a delivery system for delivering a shear-sensitive injectable material into the body of a mammal, such as a human being. The delivery system acts as a mechanical feed which continuously mixes a shear-sensitive injectable material as it delivers the shear-sensitive injectable material to a target tissue, or to a site adjacent a target tissue, within the body of a mammal. In one embodiment of the invention, the delivery system is composed of an injector system having a rotatable mixing member coupled to a driving system.

The injector system comprises an injector housing defining a lumen and having an output end coupled to a needle assembly for coupling to a needle and a driving system connection end for coupling to a drive mechanism. A mixing member extends within the lumen of the injector housing from the driving system connection end of the housing to at least the output end, and is rotatable within the lumen to feed the shear-sensitive injectable material out through the output end through the needle assembly. In a further embodiment of the invention, the injector housing comprises a feeder and a reservoir; the reservoir coupled at one end to the feeder and at the other end to a needle assembly. In this embodiment, the mixing member rotates within the feeder to feed a shear sensitive injectable material into the reservoir and moves linearly within the reservoir portion to push the shear-sensitive injectable material through the needle assembly.

A driving system is provided for use with the injector system. The driving system includes a drive mechanism in communication with an actuator which is capable of actuating the drive mechanism. An interfacing member is coupled to the drive mechanism and is for coupling to the mixing member of the injector system. In operation, the driving system is coupled to the injector system via the interfacing member. Actuation of the drive mechanism causes the mixing member to rotate within the lumen of the injector housing, thereby to mix and deliver a shear-sensitive injectable material within the injector housing through the output end of the injector housing to an injection site. In one embodiment of the invention the actuator comprises a switch and is coupled to an energy source, such as a battery, which is in electrical communication with the drive mechanism.

In another embodiment of the invention, the injector system is loaded with a shear-sensitive injectable material and is provided within a packaging to maintain the sterility of the injector system. In this embodiment, the injector system is ready to be coupled to the drive mechanism of the driving system and to be injected into the body of a mammal.

In yet another embodiment of the invention, a coupling system is provided for coupling to a tube of a syringe. The coupling system adapts the tube of the syringe to deliver a shear-sensitive injectable material into the body of a mammal. The coupling system has a coupling housing capable of mating with the tube of the syringe. A drive mechanism is positioned within the coupling housing and is capable of providing a rotary force upon actuation by the user. The coupling system also includes a mixing member which is for coupling to the drive mechanism and which extends within the tube of the syringe when the coupling housing is mated to the tube of the syringe. Upon actuation of the drive mechanism, the mixing member rotates in response to rotary force from the drive mechanism. The rotation of the mixing member simultaneously mixes and delivers a shear-sensitive injectable material loaded within the syringe. In some embodiments of the invention, the coupling housing further comprises an actuator for actuating the drive mechanism. In yet other embodiments of the invention, the coupling housing comprises finger grips for ease of manipulation of the housing and tube of the syringe during the injection process.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 3A shows a mixing member having variably spaced threads and a constant outer diameter. FIG. 3B shows a mixing member having uniformly spaced threads and a varying outer diameter. FIG. 3C shows a mixing member having both variably spaced threads and a varying outer diameter. FIG. 3D shows a mixing member having a constant outer diameter and multiple starts. FIG. 3E shows a mixing member having threads with a varying radial height and a constant outer diameter.

FIG. 6A shows the device operating in a feed mode. FIG. 6B shows the device operating in a plunger mode.

DESCRIPTION

Figure 1:
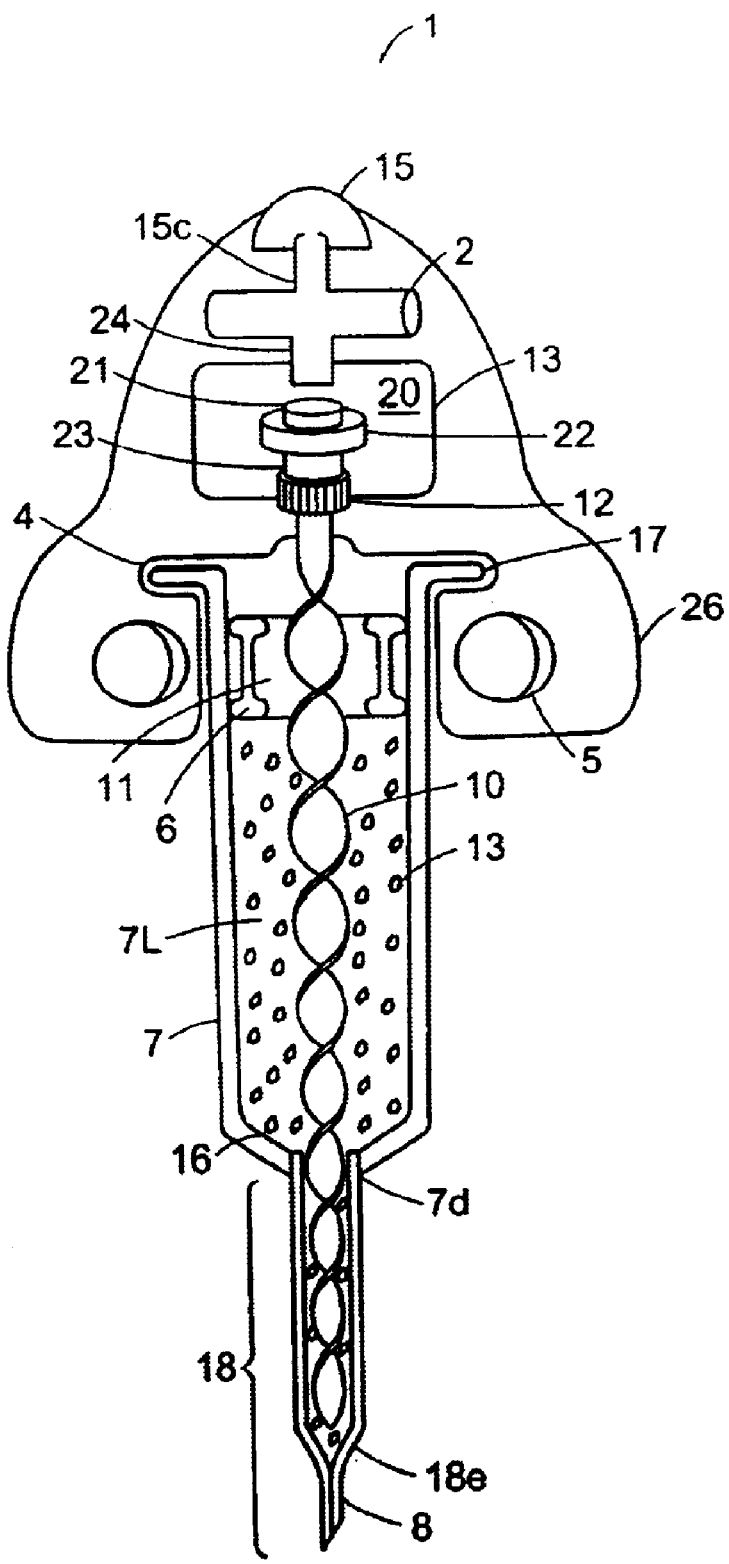
FIG. 1 shows one embodiment of a delivery system according to the invention wherein the drive system features finger grips for ease of manipulation.

Referring to FIG. 1, the delivery system 1 may be used for delivering a shear-sensitive injectable material 13 into the body of a mammal. The delivery system 1 acts as a mechanical feed to mix continuously a shear-sensitive injectable material 13 as it is delivered to a tissue or to a site adjacent to a tissue within the body of a mammal. The delivery system 1 comprises an injector system 9 (shown alone in FIG. 2) and a driving system 19 (shown alone in FIG. 4).

Figure 2:
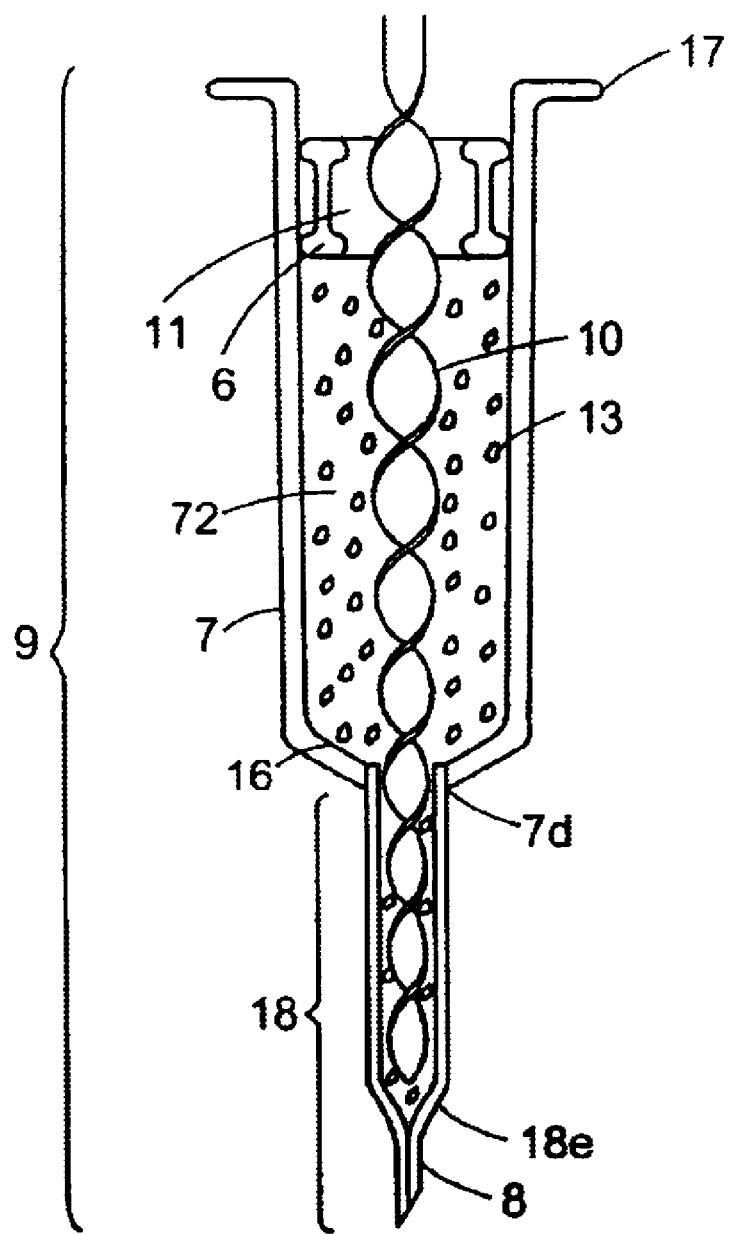
FIG. 2 is a schematic longitudinal view of one embodiment of an injector system according to the invention.

In one embodiment of the invention, and referring to FIG. 2, the injector system 9 comprises an injector housing 7 defining a lumen 7L and having an output end 16 and a driving system connection end 17. A mixing member 10 extends within the lumen 7L of the injector housing 7 from the driving system connection end 17 to at least the output end 16. The mixing member 10 rotates within the lumen 7L to mix and deliver an injectable 13 into the body of a mammal. Rotation of the mixing member causes a shear-sensitive injectable material within the lumen 7L to move forward to the output end 16 causing ejection of the shear-sensitive material through the output end 16. The output end 16 has a smaller inner diameter than the lumen 7L of the of the injector system 9.

Figure 3A:
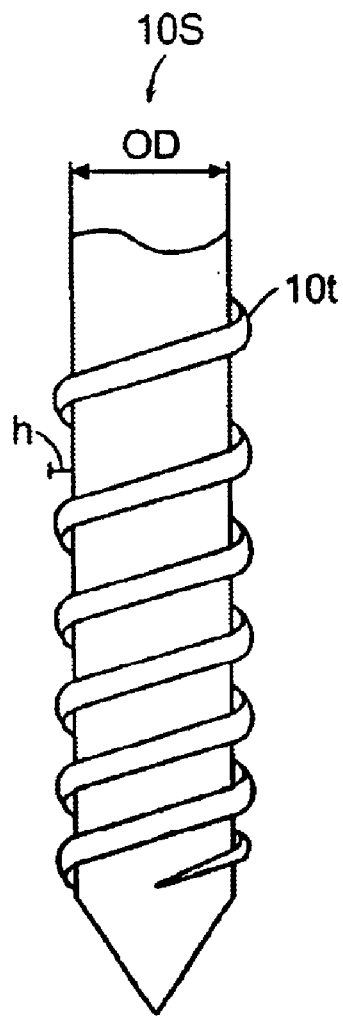
FIGS. 3A–3E show views of mixing members according to the invention.

In one embodiment of the invention, the mixing member 10 is in the form of an elongated helical element. Helical elements encompassed within the scope of the present invention include, but are not limited to, augers, screws, corkscrews, and impellers. In one embodiment, shown in FIGS. 3A–3C, the helical element is a screw 10s with a substantially conical shape which tapers in the direction of transport of the shear-sensitive injectable material 13. In a further embodiment of the invention, the screw 10s comprises threads 10t. The design of the threads 10t can be optimized to reduce erosion on the surface of the thread 10t resulting from contact with the matrix materials within the shear-sensitive injectable material 13 (e.g., by providing rounded, polished ridges).

Figure 3B:
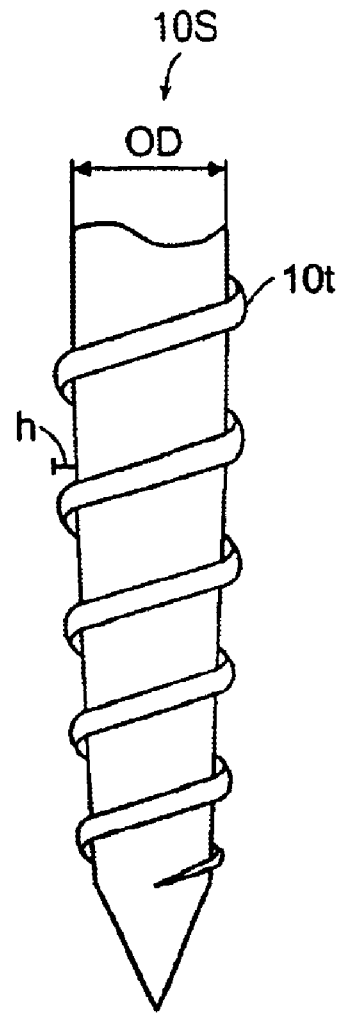
Figure 3C:
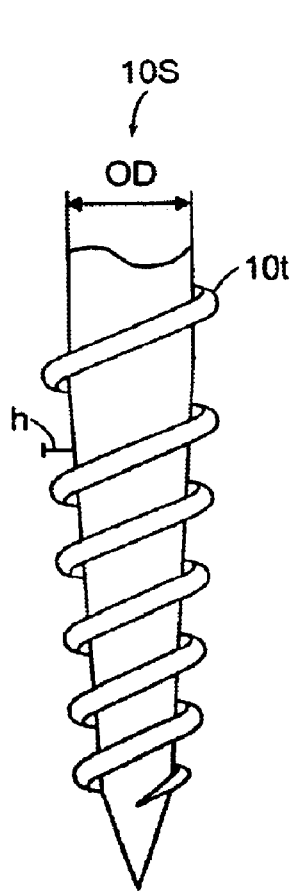

The outer diameter (OD) of the screw 10s and pitch of its threads 10t can take multiple forms depending on the delivery requirements (e.g., shear-sensitive injectabe material 13 with more matrix material requires more pressure to deliver). A helical element with a larger OD will allow increased pressure to be exerted on the shear-sensitive injectable material 13; however, this is counterbalanced by increased back-pressure from the shear sensitive injectable material 13, especially at the output end 16 of the injector system 9. In one embodiment of the invention (not shown) the OD of the screw 10s approaches the diameter of the lumen 7L. In another embodiment, shown in FIG. 3B, a screw 10s is provided having an OD which gradually decreases from the driving system connection end 17 to the output end 16 of the device, having an OD which is just slightly smaller than the diameter of the lumen 7L proximal to the driving system connection end 17. This design prevents excessive pressure on the shear-sensitive injectable material 13 at the output end 16. A similar effect may be achieved by continuously increasing the pitch of the screw 10s from the driving system connection end 17 to the output end 16 (as shown in FIG. 3B). In another embodiment of the invention, shown in FIG. 3C, both the OD and pitch of the screw 10s are varied at the same time.

Figure 3D:
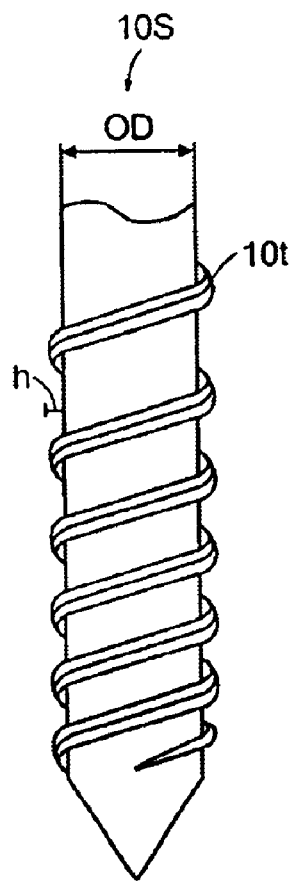
Figure 3E:
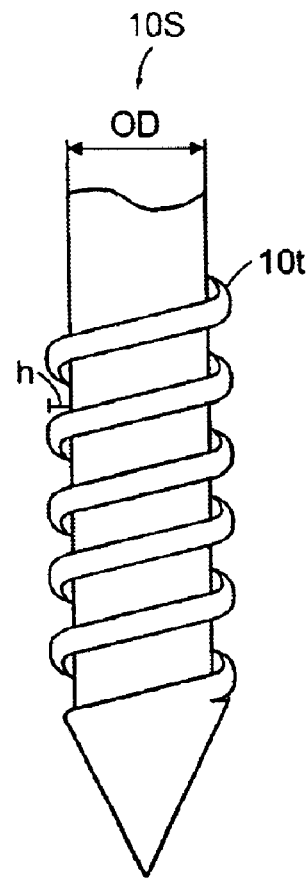

The threads 10t of the screw 10s provide channels through which the shear-sensitive injectable material 13 can flow and enhances mixing of the shear-sensitive injectable material 13 as the screw 10s rotates. The design and number of starts of the threads 10t can be varied to maximize mixing. In one embodiment, the radial height h of the threads 10t (i.e., from the base of the thread to its peak) is designed to be smallest at the driving system connection end 17 and greatest at the output end 16 to accommodate a higher proportion of unmixed matrix materials at the driving system connection end 17. The number of starts of the helical element may also be varied. In one embodiment of the invention, the threads 10t of the helical element comprise a single start (as in FIGS. 3A–3C, and 3E). In another embodiment of the invention, as shown in FIG. 3D, the threads 10t of helical element comprise multiple starts.

The mixing member 10 is positioned within the lumen 7L of the injector housing 7 by a driver guide 11. The driver guide 11 is located proximal to the driving system connection end 17 of the injector housing 7 and is held in place by a rubber stopper 6 when the injector 9 is not in use (i.e., when the mixing member 10 is not rotating). The driver guide 11 permits rotational motion of the mixing member 10, but constrains lateral motion. When the injector system 9 is in operation, the stopper 6 and driver guide 11 move downward (i.e., in the direction of the output end 16) in the direction of flow of the shear-sensitive injectable material 13. The rotational motion of the mixing member 10, and the downward movement of the stopper 6 and driver guide 11, displaces the shear-sensitive injectable material 13 within the lumen 7L and ejects it out the output end 16. The rubber stopper 6 also maintains a seal between the driver guide 11 and the inner wall of the injector housing 7, preventing leakage of the shear-sensitive injectable material 13 at the driving system connection end 17. In a further embodiment, of the invention, the injector housing 7 is marked by indices (e.g., lines or tick marks indicating units of measurement such as "cc", "ml", or "oz.") allowing the user to monitor the amount of shear-sensitive injectable material 13 being delivered.

The injector system 9 further comprises a needle assembly 18 which may be an integral part of the injector housing 7, or which may be insert-molded onto an end 7d of the injector housing 7 distal to the motor connection end 17. The needle assembly 18 further comprises a needle 8 which may be an integral part of the needle assembly 18 or may be fitted onto the end 18e of the needle assembly 18 (e.g., by screwing onto threads fabricated at the end 18e of the needle assembly 18 or by luer lock). In this embodiment of the invention, standard needles 8 used in the art may be coupled to the end 18e of the needle assembly 18. In one embodiment of the invention, the distal end of the needle 8 is reduced in diameter to allow for a constant cross-sectional area through which to deliver or feed shear-sensitive injectable material 13. The diameter of the needle 8 should be small enough to permit injection into, or adjacent to, a target site within the body (e.g., about 10 gauge to about 25 gauge).

Shear-sensitive injectable material 13 can be used to bulk-up, augment, or replace a tissue. In one embodiment, the shear-sensitive injectable material 13 is a paste-like compound comprising a crosslinked material, a carrier, and a matrix material. Suitable crosslinked materials include, but are not limited to, collagen, polymers or copolymers of acrylonitrile, vinyl acetate, methacrylate, alginates, hydrogels, polyvinylpyrrolidone, hyaluronic acid, fibrin, polygalacturonic acid, propylene glycol alginic acid, polyarabinic acids, gum cappacarrageen, polyphosphazenes, block copolymers such as polyethylene oxide-polypropylene glycol blocks, and combinations thereof. Crosslinking may be performed by exposing a crosslinkable material to changes in temperature, pH, or radiation. Chemical agents (non-ionic and ionic crosslinking agents) may also be used.

Suitable carrier materials are generally hydrophobic, and include, but are not limited to, oil, liquid polymers, liquid surfactants, and liquid plasticizers. Suitable matrix materials include, but are not limited to, fiber, chopped suture material, textured yarn material, ground suture material, ground fabric, polyester material, polytetrafluoride beads, silicon particles, polytetrafluoroethylene (PTFE) particles, ceramic particles, carbide particles, and combinations thereof. In embodiments where particles are used, particle diameters range from about 50 to about 250 microns. Ideal shear-sensitive injectable materials 13 are injectable, do not migrate a substantial distance from the injection site, and conserve their volume.

In another embodiment of the invention, bioactive materials may be additionally included with the shear-sensitive injectable material 13, such as proteins (e.g., growth factors, antibodies, ligands, receptors), naked or encapsulated nucleic acids (e.g., DNA, RNA, PNA molecules, aptamers, antisense molecules, and ribozymes), drugs, therapeutic agents, and the like. In a further embodiment of the invention, the shear-sensitive injectable material 13 is a material which may be injected into the body of mammal (e.g., a rabbit) to stimulate an immune response, i.e., such as polyacrylamide. In certain embodiments of the invention, the shear-sensitive injectable material 13 further comprises proteins, protein fragments, polypeptides (natural or synthetic), antigens, and the like.

In one embodiment of the invention, the injector system 9 is loaded with the shear-sensitive injectable material 13 and is provided within a packaging to maintain the sterility of the injector system 9. In this embodiment, the injector system 9 is ready to be coupled to the driving system 19 and the shear-sensitive injectable material 13 is ready to be injected into the body of a mammal. In general, the housing 7 of the injector system 9, including the needle assembly 18, with, or without the needle 8, is made of a material that is able to withstand conditions needed to sterilize or decontaminate it (e.g., autoclaving, irradiation, and/or exposure to chemical agents and/or anti-microbial agents) and is biocompatible. Suitable housing 7 materials include polypropylene, plastic, Teflon® material, PVC, and the like.

Figure 4:
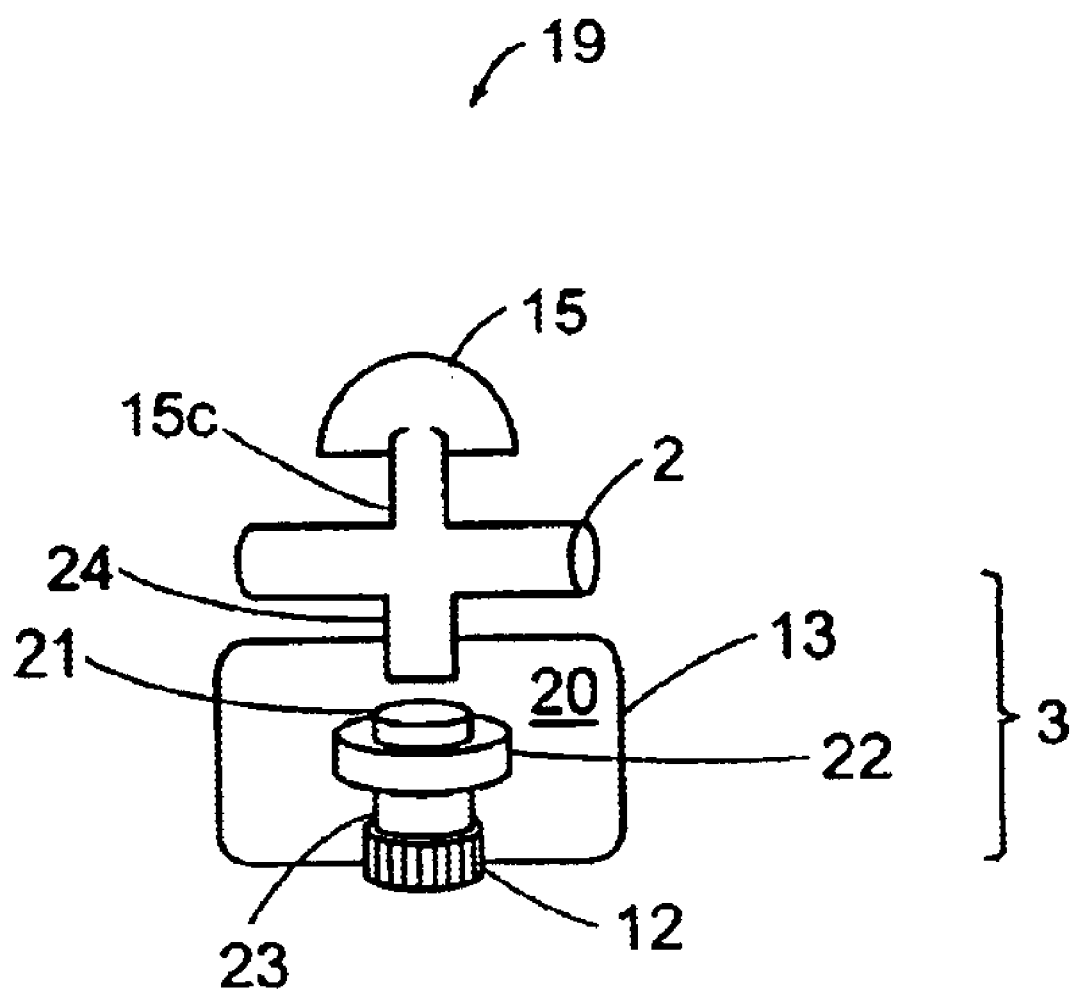
FIG. 4 shows one embodiment of a drive system according to the invention.

In a one embodiment of the invention, shown in FIG. 4, a driving system 19 is provided for use in connection with the injector system 9. The driving system 19 comprises a drive mechanism 3 in communication with an actuator 15 which is capable of actuating the drive mechanism 3. An interfacing member 12 is coupled to the drive mechanism 3 and is for coupling to the mixing member 10 of the injector system 9.

In operation, as shown in FIG. 1, the drive mechanism 3 is coupled to the injector system 9 via the interfacing member 12. In this embodiment of the invention, the delivery system 1 acts entirely in a "feed mode." Actuation of the drive mechanism 3 by the actuator 15 causes the mixing member 10 to rotate within the lumen 7L of the injector housing 7, thereby to mix and feed the shear-sensitive injectable material 13 disposed within the injector housing 7 through the output end 16 to an injection site (e.g., via the needle assembly).

Figure 5:
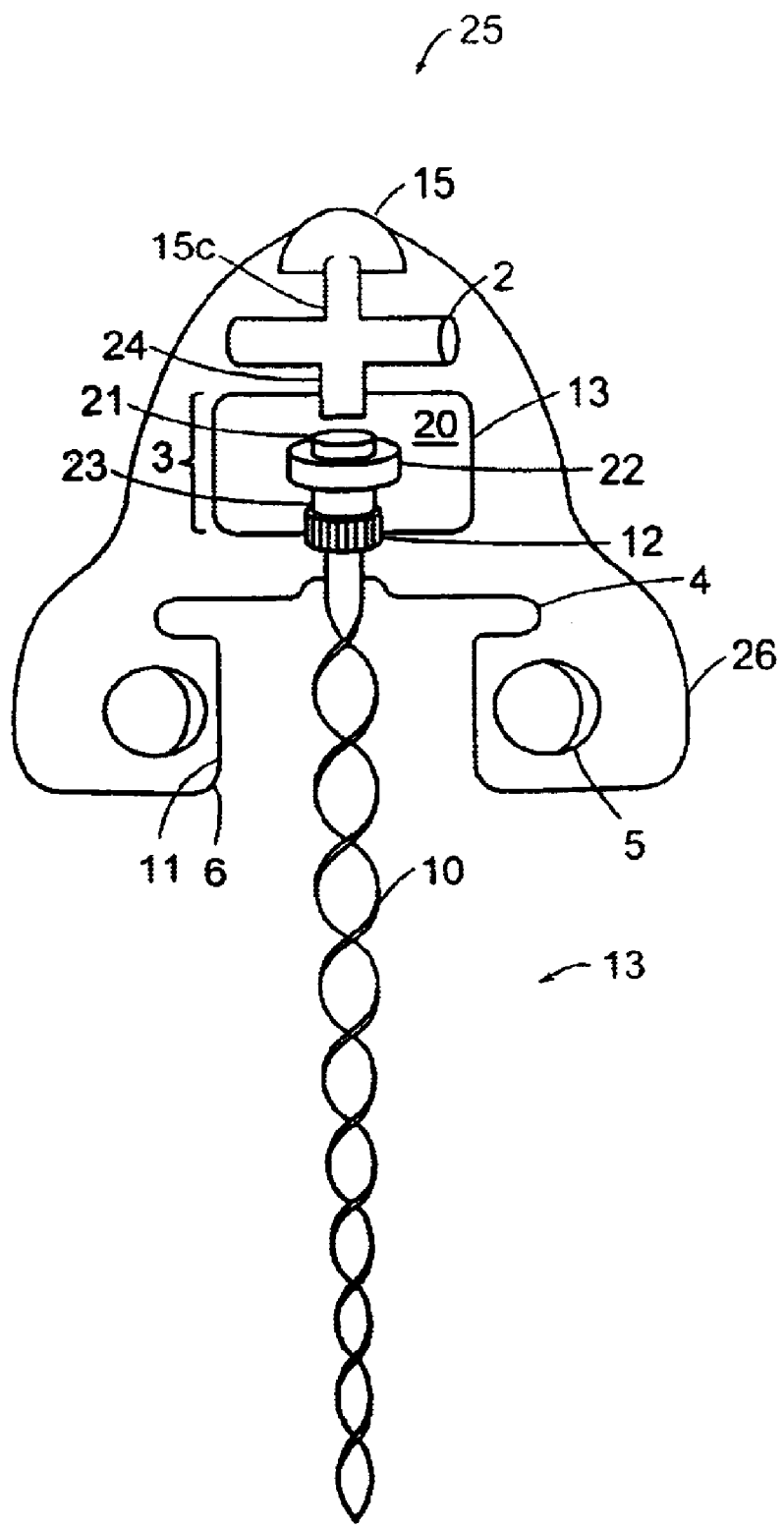
FIG. 5 shows one embodiment of a coupling system according to the invention.

In another embodiment of the invention, and referring to FIGS. 1, 4, and 5, the drive mechanism 3 is a motor which is contained within a motor housing 13 and includes a shaft 23 which is adapted for coupling to the interfacing member 12. In this embodiment of the invention, mechanical rotary force from the shaft 23 is transmitted through the interfacing member 12 to the mixing member 10, thereby rotating the mixing member 10 within the lumen 7L of the injector 9.

In one embodiment of the invention, shown in FIG. 4, the drive mechanism 3 comprises an electric motor 20 which includes a conducting loop 22 mounted on a shaft 23 made of insulating material. A magnetic field around the loop 22, supplied by a magnet 21, causes the loop 22 to rotate when a current flows through it. The loop 22 causes the shaft 23 to rotate, transmitting rotary force to the mixing member 10 via the interfacing member 12. In another embodiment of the invention, the electric motor 20 is a DC motor and further comprises a commutator (not shown) for switching the direction of an electric current to maintain the shaft 23's direction of motion. In another embodiment of the invention, the drive mechanism 3 comprises a stationary loop 22 and a movable magnet 21. In a further embodiment of the invention, the motor 20 is a high torque low speed DC motor controlled by a switch.

The drive mechanism 3 may further include electrical connection elements 24 for connecting the motor 20 to an energy source 2, such as a battery. In one embodiment of the invention, shown in FIG. 4, the flow of energy (e.g., current) from the energy source 2 is controlled by an actuator 15 to which it is coupled by electrical elements 15c. In a further embodiment of the invention, the actuator 15 comprises a switch which can be turned on and off by an operator.

Figure 6A:
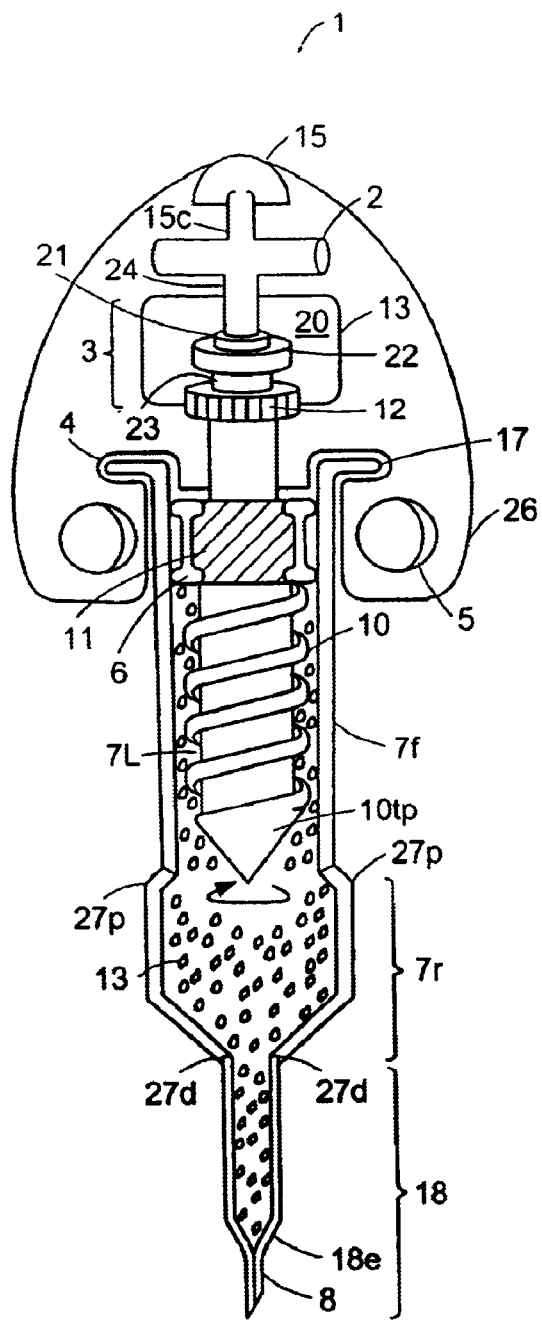
FIGS. 6A–B show an embodiment of a delivery system which is capable of operating in both a feed mode and a plunger mode.
Figure 6B:
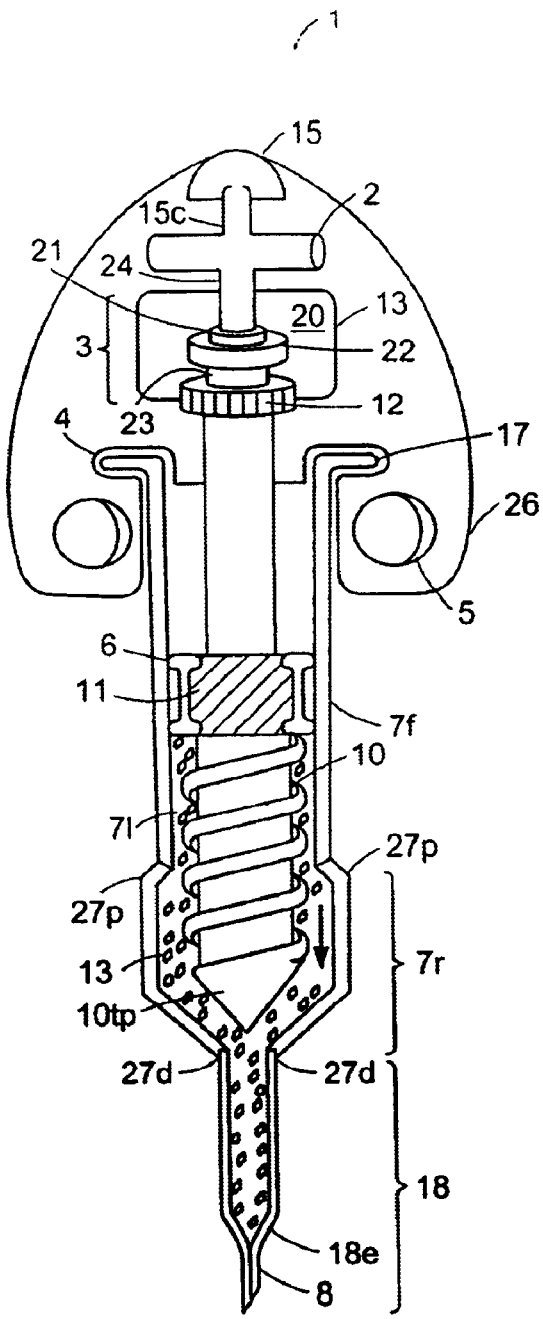

In another embodiment of the invention, shown in FIGS. 6A–B, the delivery system 1 may be operated in both a feed mode and a "plunger mode." In this embodiment, the housing of the injector system defines a feeder 7f and a reservoir 7r. The reservoir 7r has a proximal end 27p and a distal end 27d. The proximal end 27p of the reservoir 7r is coupled to the end of feeder 7f distal from the driving system connection end 17 while the distal end 27d of the reservoir is coupled to the needle assembly 18. In one embodiment of the invention, the feeder 7f and reservoir 7p comprise a single unit molded together, while in another embodiment of the invention, the reservoir 7r is a module which can be separated from the feeder 7f.

During the feed mode of operation, shown in FIG. 6A, the tip 10tp of the mixing member 10 terminates within the feed portion 7f of the delivery system 1. Rotation of the mixing member 10 within the feed portion 7f by the drive mechanism 3 then feeds the shear-sensitive injectable material 13 into the reservoir portion 7r of the delivery system 1. During the plunger mode of operation, shown in FIG. 6B, a linear force is exerted on the mixing member 10, either manually, mechanically, or through the use of the drive mechanism 3, and the mixing member 10 is used as a plunger to push shear-sensitive injectable material 13 within the reservoir 7r through the needle assembly 18. This embodiment of the invention allows more force to be developed at the needle assembly 18 portion of the device, making it easier to inject the shear-sensitive injectable material 13 into a target tissue.

In a further embodiment of the invention, shown in FIG. 5, a coupling system 25 is provided for coupling to a tube of a syringe. The coupling system 25 is for adapting the tube of the syringe to deliver a shear-sensitive injectable material 13 into the body of a mammal. The coupling system 25 comprises a coupling housing 26 capable of mating with the tube of the syringe at mating portion 4 of the coupling housing 26 (e.g., by a twisting and locking motion). A drive mechanism 3 is positioned within the coupling housing 26 and is capable of providing a rotary force upon actuation. The coupling system 25 also includes mixing member 10 which is for coupling to the drive mechanism 3 via interfacing member 12 and which extends within the tube of the syringe when the coupling housing 26 is mated to the tube of the syringe.

Upon actuation of the drive mechanism 3, the mixing member 10 rotates in response to force from the drive mechanism 3. The rotation of the mixing member 10 within the lumen 7L simultaneously mixes and delivers a shear-sensitive injectable material 13 loaded within the tube of the syringe. In another embodiment of the invention, the coupling housing 26 further comprises an actuator 15 for actuating the drive mechanism 3.

It should be apparent to those of skill in the art that the exact configuration of the housing 26 may be modified in many ways without affecting the operation of the coupling system 25. In one embodiment of the invention, the coupling housing 26 comprises finger grips 5 for ease of manipulation of the coupling system 25 and syringe during the injection procedure, and can be manipulated with one or both hands. In another embodiment of the invention, a high torque low speed DC torque motor 20 is provided within the coupling housing 26. The motor 20 is actuatable by a switch that an operator can easily manipulate with a thumb while gripping the outside of the coupling housing 26. The intent is to provide an ergonomic feel to the user so that he or she may have or perceive control of the flow rate of material 13 exiting the syringe.

Although the mixing member 10 is shown coupled to the interfacing member 12 in FIGS. 5, 6A and 6B, the various components of the coupling system 25 may be provided separately, i.e., in the form of a kit, which may optionally include the tube of a syringe. The tube of the syringe may further be provided in a sterile or sterilizable packaging. In another embodiment of the invention, the mixing member 10 may be provided as part of the injector system 9, and may additionally include the shear-sensitive injectable material 13. Any of the injector system 9, or injector system 9 with shear-sensitive injectable material 13, may also be provided within a sterile or sterilizable packaging.

The coupling system 25 of the present invention may be adapted for coupling to a variety of standard sized syringes known in the art, from 1 cc to 50 cc. In one embodiment of the invention, the coupling system 25 is adapted for coupling to the injector system 9 discussed above, which may also be molded to a variety of sizes, and which may include indicia against which to measure the amount of shear-sensitive injectable material 13 being delivered (e.g., markings indicating "ml," "cc," or "oz." When injecting a shear-sensitive injectable material 13 to bulk-up, augment or replace tissue, a syringe or injector system 9 is selected which is capable of delivering an amount of shear-sensitive injectable material 13 suitable for a desired medical procedure. For example, the amount of material used for augmentation of anal sphincters is generally from 14–40 cc, and typically from about 20–30 cc, while the amount of shear-sensitive injectable material 13 that is used for muscle repair is typically from about 5 to about 10 cc.

Although the delivery system 1 of the present invention is particularly suited for the delivery of a shear-sensitive injectable material 13, because of its ability to act as a mechanical feed, it should be readily apparent to those of skill in the art, that the system may be used to deliver a variety of injectable materials, including fluids, to a target site.

Having thus described certain embodiments of the present invention, various alterations, modifications, and improvements will be apparent to those skilled in the art. Such variations, modifications, and improvements are intended to be within the spirit and scope of the invention. The materials employed, as well as their shapes and dimensions, generally can vary. Accordingly, the foregoing description is by way of example only and is not intended to be limiting.

What is claimed is:

1. An injector system, comprising:
   a housing defining a lumen and having an output end and a driving system connection end, the lumen comprising a proximal portion and a distal portion and the inner diameter of the proximal portion being substantially larger than the inner diameter of the distal portion;
   a mixing member extending within the lumen from the driving system connection end to at least the output end, the mixing member being rotatable within the lumen in both the proximal portion and the distal portion; and
   a needle assembly coupled to the output end of the housing, for coupling to a needle.

2. The injector system of claim 1, wherein the mixing member comprises a helical element.

3. The injector system of claim 2, wherein the helical element is an auger.

4. The injector system of claim 1, further comprising a driver guide, the driver guide positioning the mixing member within the lumen.

5. The injector system of claim 1, wherein the needle assembly is coupled to a needle.

6. The injector system of claim 1, further comprising an injectable material.

7. The injector system of claim 6, wherein the injectable comprises a shear-sensitive injectable material.

8. The injector system of claim 7, wherein the shear-sensitive injectable material comprises a cross-linked material, a carrier, and a matrix material.

9. The injector system of claim 7, wherein the injectable material further comprises a bioactive molecule.

10. The injector system of claim 7, wherein the housing comprises a feeder portion and a reservoir portion, and wherein the mixing member is rotatable within the feeder portion and can move linearly within the reservoir portion.

11. The injector system of claim 1, wherein the lumen further comprises a middle portion having an inner diameter substantially larger than the inner diameter of the proximal portion.

12. The injector system of claim 1 wherein the mixing member comprises a screw having a proximal end and a distal end, the screw being-extendable and rotatable within both the proximal portion and the distal portion of the lumen, the injector system further comprising a drive mechanism coupled to the proximal end of the screw, to rotate the screw when the drive mechanism is actuated.

13. The injector system of claim 12, further comprising an actuator, the actuator coupled to the drive mechanism to actuate the drive mechanism.

14. The injector system of claim 12, wherein an outer diameter of the screw decreases from the proximal end to the distal end.

15. The injector system of claim 12, wherein a pitch of the screw increases from the proximal end to the distal end.

16. The injector system of claim 12, wherein a radial thread height of the screw increases from the proximal end to the distal end.

* * * * *

UNITED STATES PATENT AND TRADEMARK OFFICE
CERTIFICATE OF CORRECTION

PATENT NO. : 6,699,214 B2  Page 1 of 1
DATED : March 2, 2004
INVENTOR(S) : Barry N. Gellman It is certified that error appears in the above-identified patent and that said Letters Patent is hereby corrected as shown below:

<u>Column 8,</u>
Line 53, after "injectable", insert -- material --.

Signed and Sealed this

Fourteenth Day of December, 2004

JON W. DUDAS
*Director of the United States Patent and Trademark Office*